(12) United States Patent
Popowska et al.

(10) Patent No.: US 9,012,200 B2
(45) Date of Patent: Apr. 21, 2015

(54) COMPOSITION OF BACTERIAL STRAINS, BIOREMEDIATION MIXTURE AND USE OF THIS COMPOSITION FOR THE REMOVAL OF CONTAMINANTS FROM THE SOIL AND THE METHOD FOR PURIFYING THE SOIL CONTAMINANTS

(71) Applicant: Uniwersytet Warszawski, Warsaw (PL)

(72) Inventors: Magdalena Popowska, Warsaw (PL); Hanka Boszczyk-Maleszak, Warsaw (PL); Iga Komorowska, Warsaw (PL)

(73) Assignee: Uniwersytet Warszawski, Warsaw (PL)

( * ) Notice: Subject to any disclaimer, the term of this patent is extended or adjusted under 35 U.S.C. 154(b) by 0 days.

(21) Appl. No.: 14/163,711

(22) Filed: Jan. 24, 2014

(65) Prior Publication Data

US 2014/0141494 A1 May 22, 2014

Related U.S. Application Data

(63) Continuation-in-part of application No. PCT/IB2013/001060, filed on May 28, 2013.

(30) Foreign Application Priority Data

May 31, 2012 (PL) .......................... 399388

(51) Int. Cl.
| | |
|---|---|
| *C12N 1/20* | (2006.01) |
| *B09C 1/10* | (2006.01) |
| *C12R 1/38* | (2006.01) |
| *C12R 1/06* | (2006.01) |
| *C12R 1/01* | (2006.01) |

(52) U.S. Cl.
CPC ... *B09C 1/10* (2013.01); *C12R 1/38* (2013.01); *C12R 1/06* (2013.01); *C12R 1/01* (2013.01); *C12N 1/20* (2013.01)

(58) Field of Classification Search
None
See application file for complete search history.

(56) References Cited

U.S. PATENT DOCUMENTS 5,773,283 A * 6/1998 Pierce ........................ 435/262

FOREIGN PATENT DOCUMENTS

EP 0 589 818 3/1994

OTHER PUBLICATIONS

Reddy et al., Environmental Engineering Science, 2011, vol. 28, No. 6, p. 405-413.*
Seo et al., Int. J. Environ. Res. Public Health, 2009, vol. 6, p. 278-309.*
Zhao et al., Canadian Journal of Microbiology, 1999, vol. 45, No. 5, p. 427 Only.*
S. Labana, et al., A Microcosm Study on bioremediation of p-Nitrophenol-Contaminated Soil Using Arthrobacter Protophormiae RKJ100, App. Microbiol. Biotechnol (2005) vol. 68, p. 417-424.
Zheng Liu, et al., Biodegradation of p-Nitrophenol and 4-Chlorophenol by *Stenotrophomonas* sp., FEMS Microbiol Lett (2007) vol. 277, p. 150-156.
G. Pandey, et al., Monitoring Arthrobacter Protophormiae RKJ100 in a 'Tag and Chase' Method During p-Nitrophenol Bio-Remediation in Soil Microcosms, Appl. Microbiol. Biotechnol. (2006) vol. 70, p. 757-760.
Ben A. Stenuit, et al., Microbial 2,4,6-Trinitrotoluene Degradation: Could We Learn From (Bio) Chemistry for Bioremediation and Vice Versa? Appl. Microbiol. Biotechnol. (2010) vol. 88, p. 1043-1064.
Chao Wang, et al., Bioremediation of Nitrobenzene-Polluted Sediments by *Pseudomonas putida*, Bull Environ. Contam. Toxicol. (2009) vol. 83, p. 865-868.

* cited by examiner

*Primary Examiner* — Kade Ariani
(74) *Attorney, Agent, or Firm* — Vedder Price P.C.; Thomas J. Kowalski; Deborah L. Lu

(57) ABSTRACT

The object of the present invention is a composition of bacterial strains which may comprise *Stenotrophomonas* sp. strain 2L, *Stenotrophomonas* sp. strain 5L, *Stenotrophomonas* sp. strain 6L, *Stenotrophomonas* sp. strain 3N, *Achromobacter* sp. strain 4P, *Arthrobacter* sp. strain 1N, *Brevundimonas* sp. strain 2N, *Brevundimonas* sp. strain 5N, *Brevundimonas* sp. strain 6N, *Pseudomonas* sp. strain 3G, and *Pseudomonas* sp. strain 4, deposited under the number KKP 2041p (IAFB Collection of Industrial Microorganisms—Institute of Agricultural and Food Biotechnology in Warsaw), a bioremediation vaccine (bioremediation mixture) which may comprise the composition of these strains, the use of the vaccine in the removal of contaminants from the soil, and the method for the treatment of contaminated soil.

26 Claims, 1 Drawing Sheet

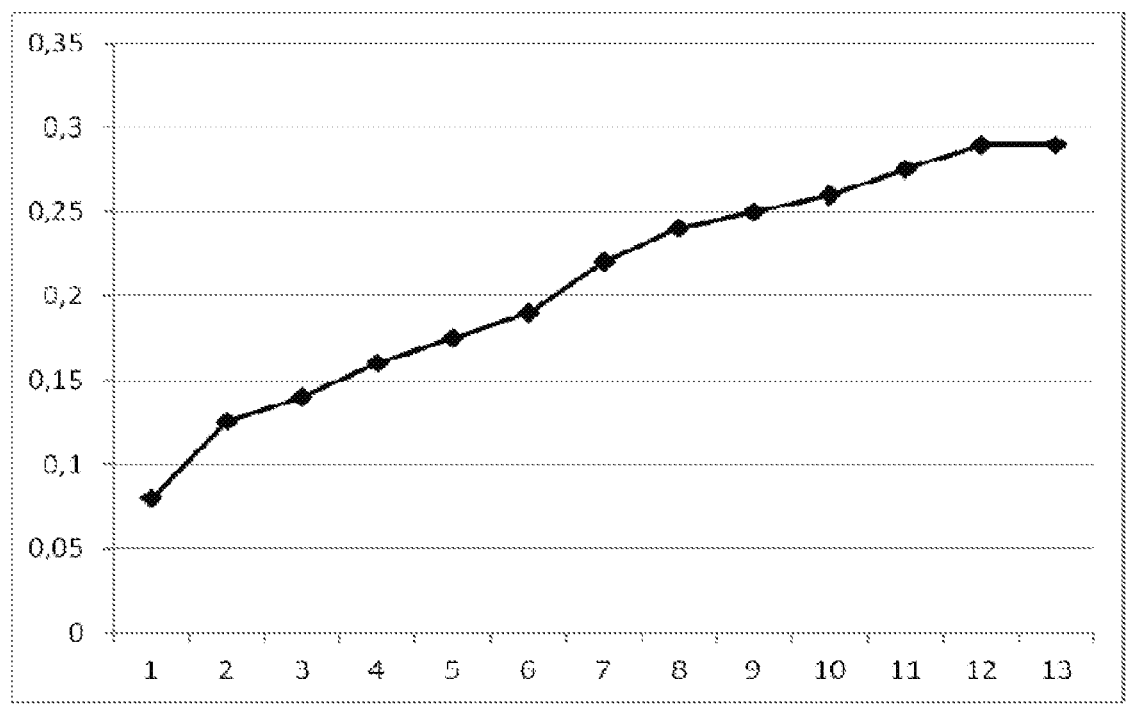

COMPOSITION OF BACTERIAL STRAINS, BIOREMEDIATION MIXTURE AND USE OF THIS COMPOSITION FOR THE REMOVAL OF CONTAMINANTS FROM THE SOIL AND THE METHOD FOR PURIFYING THE SOIL CONTAMINANTS

RELATED APPLICATIONS AND INCORPORATION BY REFERENCE

This application is a continuation-in-part application of international patent application Serial No. PCT/B2013/001060 filed May 28, 2013, which published as PCT Publication No. WO 2013/179116 on Dec. 5, 2013, which claims benefit of Polish patent application Serial No. P.399388 filed May 31, 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

This invention relates to a composition of 11 strains: *Stenotrophomonas* sp. strain 2L, *Stenotrophomonas* sp. strain 5L, *Stenotrophomonas* sp. strain 6L, *Stenotrophomonas* sp. strain 3N, *Achromobacter* sp. strain 4P, *Arthrobacter* sp. strain 1N, *Brevundimonas* sp. strain 2N, *Brevundimonas* sp. strain 5N, *Brevundimonas* sp. strain 6N, *Pseudomonas* sp. strain 3G, and *Pseudomonas* sp. strain 4G, deposited under the number KKP 2041p., a bioremediation vaccine (bioremediation mixture) comprising a composition of these bacterial strains, the use thereof in the removal of contaminants from soil, as well as a method of soil treatment.

BACKGROUND OF THE INVENTION

The continuous development of industry relates to the appearance in the environment of chemical compounds which under normal conditions do not occur there. At present, nitro compounds are amongst the major types of anthropogenic pollution, among which nitrobenzene, 2- and 4-nitrotoluene, 3-nitrotoluene, 4-nitrophenol, 3-nitrophenol and p-nitroaniline deserve particular attention. They are used in the manufacture of explosives, in pesticide and herbicide production, as substrates in the synthesis of dyes, plastics, paints, as well as in the pharmaceutical industry. It is estimated, that each year about $10^8$ tons of organic nitro compounds are produced in the world, and more than 8.5 tons of nitrobenzene alone are released into the environment. For almost 80 years the widespread use of these compounds in many branches of the industry, as well as the production of massive amounts of military materials and ammunition in the first half of the previous century in connection with the two world wars have contributed to the serious contamination of the environment with nitro compounds. The aforementioned types of compounds and their metabolites are highly toxic and dangerous to humans. Some of them are potent poisons, often with strong mutagenic and carcinogenic properties. Most of the aromatic nitro compounds are characterised by their stability and persistence in biological systems, and their considerable resistance to degradation (Kulkarni and Chaudhari, 2007).

An additional concern is the fact that the contamination of soil with nitro compounds, is also a direct threat to groundwater, and consequently may result in the penetration of these pollutants into flowing waters. The problem of soil and groundwater contamination with organic compounds from various branches of the industry, concerns not only Poland and other European Union countries, but practically all industrialized countries of the world. Both in Poland and worldwide, the problem of environmental pollution with these compounds concerns mainly the areas surrounding chemical plants, where they were used as substrates in organic synthesis, as well as the areas of military bases, where they were kept and stored.

There are several conventional methods of physico-chemical neutralization of nitro compounds, such as oxidation and photo-oxidation, hydrolysis, evaporation, combustion, adsorption, etc. (Kanekar et al., 2003). Such methods, however, have numerous drawbacks and limitations. Combustion is not cost-effective nor environmentally friendly. Additionally, it is accompanied by the release of considerable amounts of toxic fumes into the environment. During such procedures as filtration, extraction or adsorption on resin, the undesirable compounds are only separated, and this does not lead to their breakdown. Oxidation processes, meanwhile, generate the formation of toxic derivatives and are associated with high costs (Kulkarni and Chaudhari, 2007).

Several land remediation strategies, based on physical, chemical and biological methods were developed. It is believed, however, that bioremediation technologies that are the most inexpensive and most effective and thus safe are ones, utilizing the metabolic potential of microorganisms.

Bioremediation is a process of repair, in which microorganisms such as bacteria, yeasts and filamentous fungi are used to decompose hazardous substances to less toxic or non-toxic compounds.

For the purposes of bioremediation processes, microorganisms are isolated from the natural microflora present in the contaminated environment (reinoculation), or are obtained by methods of genetic engineering. In practice, in the biodegradation process, specialized kits (consortia of microorganisms) showing particular abilities to degrade certain groups of hydrocarbons are involved. Such consortia, apart from the high detoxification activity, must quickly adapt to the contaminated environment, cooperate with the indigenous microflora and not to accumulate toxic decomposition intermediates.

Two types of microbiological preparations can be distinguished: preparations containing strains of external origin and autovaccines containing effective indigenous strains, isolated from treated soil using various methods.

Patent PL 180 141 discloses a method of microbiological remediation of petroleum-contaminated soils, in which indigenous microorganisms isolated from soil intended to undergo treatment, are utilized. The isolated strains of bacteria are grown under aerobic conditions in a liquid mineral medium supplemented with petroleum hydrocarbons, and after identification, bacteria with the highest activity in degrading these pollutants are selected. The selected 5 to 10 different species of bacteria, are grown at 26° C. for 48 to 72 hours. The propagated culture is introduced into the contaminated soil, by spraying it with an aqueous suspension of bacteria, with more than $10^5$ cells per 1 g of dry soil.

Patent PL 189 586 discloses the method of preparation of an autovaccine that accelerates the treatment of soil and waste water contaminated with petroleum, which relies on the isolation of bacteria from soil and waste waters through dilution and selective culturing in media enriched with sterile crude oil or naphthalene as the sole carbon source.

Prolonged presence of aromatic nitro compounds, particularly nitroaniline, nitrobenzene and nitrophenol in soil initiates the process of natural adaptation and selection of microorganisms in the contaminated area, which affects the quality, as well as the species composition of autochthonic (native to a given ecosystem) groups of microorganisms. Effective bioremediation requires, apart from the accurate knowledge of the microorganisms responsible for the degradation of given aromatic nitro compounds, the understanding of the degradation pathways of these compounds, at the physiological, biochemical, and molecular levels, as well as research on the optimization of conditions necessary for the smooth running of the bioremediation processes. Such studies have been carried out by the Authors of the present solution.

In soils from military sites (i.a. military training grounds) and industrialized areas, high concentrations of not only a variety of organic xenobiotics, but also of heavy metals such as arsenic, cadmium, chromium, copper, lead, mercury, nickel, zinc and others are very often reported (Bahig and Altalhi, 2009). Heavy metals are considered to be potent inhibitors of organic xenobiotic biodegradation processes (Silva et al., 2007). It is thought that the presence of heavy metals in industrial waste waters is one of the main factors limiting the use of biological remediation methods (Kulkami and Chaudhari, 2007). The long-term presence of these pollutants in the environment, however, resulted in bacteria developing mechanisms of detoxifying these compounds. Furthermore, it is suggested that microbial tolerance to heavy metals can affect the maintenance and passing of antibiotic resistance genes between bacteria, by increasing the selective pressure of the environment (Spain, 2003). There is also evidence of a connection between the resistance of bacteria to many clinically important classes of antibacterial drugs, heavy metals and quaternary ammonium compounds used as disinfectants. In many cases, this is related to the location of genes that determine such resistance, in close proximity on the same bacterial plasmid, suggesting the possibility of passing of whole gene clusters by horizontal gene transfer (Schluter et al., 2007).

There are numerous studies concerning the process of bioremediation of various xenobiotics polluting soil e.g. crude oil and its derivatives, but, at the current state of the art, there are no studies concerning the use of in situ bioremediation of areas contaminated with aromatic nitro compounds. In the professional literature on biodegradation of cyclic nitro compounds, this problem has been considered and analysed only on the laboratory scale. The application of an effective method of nitro compound biodegradation, particularly of nitroaniline, seems to be the optimal solution in many respects, primarily because these are processes that occur naturally in the environment, but also, what is of great importance, they are very efficient and are associated with lower costs than traditional methods such as physico-chemical techniques.

Polish patent PL 380 007 relates to a method of soil bioremediation and prevention of the spreading of contamination with organic substances, based on the introduction of a yeast species *Yarrowia lipolytica* in an immobilised form into the soil. The yeast are introduced directly into the contaminated areas or around them, using an in situ method in the torr of a vaccine (biological preparation) on an organic medium, which is sodium alginate, agar, gelatine, collagen or bird feathers. The vaccine, in a liquid or dry form, may be introduced as granules or a biofilm or biogel, and the yeast constitute from 5 to 50% of the vaccine (by mass), wherein the vaccine may constitute from 10 to 100% of the material introduced into the soil. The vaccine is placed at a depth of 0.1 to 2 m into holes of a diameter of 0.1 to 1.0 m, whereas their distribution may be linear or transversely-overlapping or concentric or encircling the given area or situated at its lowest point, according to the direction of groundwater flow, and in the case of the protection of water bodies, near the shoreline, beyond the reach of the waves. The invention can find use especially in areas contaminated by petroleum compounds, oil industry wastes, vegetable and mineral oils.

Citation or identification of any document in this application is not an admission that such document is available as prior art to the present invention.

SUMMARY OF THE INVENTION

The present solution is a natural method of removing hazardous pollutants from the environment without introducing any synthetic products into it. The it situ bioremediation is based on natural processes occurring in the environment, which is associated with considerably lower costs than conventional physico-chemical methods. The developed and deposited composition of strains (vaccine) facilitates the quick acquisition of the appropriate amount of the formulation and conduction of bioremediation in a short time.

Bacterial strains which are part of the composition of the bioremediation vaccine, being the object of this invention, are able to degrade/metabolise aromatic nitro compounds and, in general, aromatic compounds such as phenols, aminophenols, nitrophenols as well as polycyclic aromatic compounds, which may be used by these microorganisms as the sole source of carbon and energy. Furthermore, the strains are able to grow in the presence of high concentrations of heavy metals (and heavy metals are also present in the case of soils contaminated with organic nitro compounds or petroleum). They are simultaneously, able to grow in the presence of high concentrations of antibiotics (in cases of bioremediation of areas near pharmaceutical companies or additionally contaminated with antibiotics or their metabolites this is highly significant); the antibiotics being from the following groups: macrolides (erythromycin), aminoglycosides (streptomycin), fluoroquinolones (ciprofloxacin), tetracyclines (tetracycline), beta-lactams glycopeptides vancomycin).

The aim of this invention is the efficient way of removing toxic aromatic nitro compounds with the use of a microbiological bioremediation mixture (vaccine) for the bioremediation of soil contaminated with aromatic nitro compounds.

The object of the invention is a composition of strains comprising: *Stenotrophomonas* sp. strain 2L, *Stenotrophomonas* sp. strain 5L, *Stenotrophomonas* sp. strain 6L, *Stenotrophomonas* sp. strain 3N, *Achromobacter* sp. strain 4P, *Arthrobacter* sp. strain 1N, *Brevundimonas* sp. strain 2N, *Brevundimonas* sp. strain 5N, *Brevundimonas* sp. strain 6N, *Pseudomonas* sp. strain 3G, and *Pseudomonas* sp. strain 4G, deposited under the number KKP 2041p, (IAFB Collection of Industrial Microorganisms—Institute of Agricultural and Food Biotechnology in Warsaw, Poland).

It is preferable that at least one strain of the composition, more preferably all of the strains, show resistance to antibiotics from the following groups: aminoglycosides, fluoroquinolones, glycopeptides, macrolides, penicillins, sulphonamides, tetracyclines.

It is preferable that at least one strain of the composition, more preferably all of the strains, show resistance to ciprofloxacin.

It is preferable that at least one strain of the composition, more preferably all of the strains, show resistance to erythromycin.

It is preferable that at least one strain of the composition, more preferably all of the strains, show resistance to gentamicin.

It is preferable that at least one strain of the composition, more preferably all of the strains, show resistance to penicillin.

It is preferable that at least one strain of the composition, more preferably all of the strains, show resistance to streptomycin.

It is preferable that at least one strain of the composition, more preferably all of the strains, show resistance to sulfamethoxazole.

It is preferable that at least one strain of the composition, more preferably all of the strains, show resistance to tetracycline.

It is preferable that at least one strain of the composition, more preferably all of the strains, show resistance to vancomycin.

It is preferable that at least one strain of the composition, more preferably all of the strains, show resistance to heavy metals, such as As (III), Cu (II), Cr (VI), Zn (II) and Ni (II).

Another object of the present invention is a bioremediation vaccine (bioremediation mixture) comprising the composition of strains as described above.

Preferably, the vaccine may comprise $10^5$ bacteria cells in ml of medium.

Preferably, apart from the composition of 11 strains, the vaccine may comprise a liquid mineral medium supplemented with a nitro compound as the sole source of carbon.

Preferably, apart from the composition of 11 strains, the vaccine may comprise a solid mineral medium supplemented with a nitro compound as the sole source of carbon.

Preferably, the nitro compound in the medium is nitrobenzene, p-nitroaniline, 2-nitrotoluene, 4-nitrotoluene, dinitrotoluenes, trinitrotoluenes, mononitrophenols or polynitrophenols.

Preferably, the source of carbon in the medium is at least one of the above nitro compounds.

Preferably, the nitro compound is added in amounts of 50-200 mg/L to the culture medium, depending on the degree of contamination of the soil.

Another object of the invention is the use of the bioremediation vaccine to remove contaminants in the form of aromatic nitro compounds from the soil.

Another object of invention is a method for the treatment of contaminated soil through the use of the vaccine, based on the isolation of soil microorganisms from the contaminated soil, their culture, selection/identification of the microorganisms, and then growth of the selected soil microorganisms, thereafter the propagated culture is introduced into the polluted soil, which is mechanically oxygenated and its moisture is kept at an appropriate level, characterised by the fact that the aromatic nitro compounds are removed from the contaminated soil, and soil microorganisms are a part of the composition of strains as described above.

Preferably, the method takes place in situ.

Preferably, the method takes place ex situ.

Preferably, the cultures are propagated on a liquid mineral medium supplemented with a nitro compound as the sole source of carbon.

Preferably, the cultures are propagated on a solid mineral medium supplemented with a nitro compound as the sole source of carbon.

Preferably, the nitro compound in the medium is nitrobenzene, p-nitroaniline, 2-nitrotoluene, 4-nitrotoluene, dinitrotoluenes, trinitrotoluenes, mononitrophenols or polynitrophenols.

Preferably, the source of carbon in the medium is at least one of the above nitro compounds.

Preferably, the nitro compound is added in amounts of 50-200 mg/L to the culture medium, depending on the degree of contamination of the soil.

Preferably, the culture is propagated at temperatures between 20-25° C.

Preferably, the contaminated soil is sprayed with the suspension of bacteria (bioremediation vaccine) in a volume ratio of the vaccine to soil in the range of 1:10 to 3:10.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with the IAFB Collection of Industrial Microorganisms—Institute of Agricultural and Food Biotechnology in Warsaw, under deposit accession number KKP 2041p were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

FIG. 1, presents the growth of a mixed culture of bacteria (11 strains) in a liquid medium (M9) supplemented with aromatic nitro compound.

DETAILED DESCRIPTION OF THE INVENTION

The use of the composition being the object of the present invention is a natural method, which does not introduce any synthetic products into the environment. The fact that the object of the present solution is composed of autochthonic organisms shortens the time required for biodegradation. Moreover, the method is based on processes naturally occurring in the environment, which are effective and more efficient than, for example, physico-chemical methods.

Microorganisms were isolated from soil contaminated with nitro compounds (former military training site in Pomerania).

For the purposes of the solution, the strains were designated as follows:

TABLE 1

| Designation of the strains | |
|---|---|
| 2L | *Stenotrophomonas* sp. |
| 5L | *Stenotrophomonas* sp. |
| 6L | *Stenotrophomonas* sp. |
| 4P | *Achromobacter* sp. |
| 3G | *Pseudomonas* sp. |
| 4G | *Pseudomonas* sp. |
| 1N | *Arthrobacter* sp. |
| 2N | *Brevundimonas* sp. |
| 3N | *Stenotrophomonas* sp. |
| 5N | *Brevundimonas* sp. |
| 6N | *Brevundimonas* sp. |

The object of the present invention has been presented in the following unlimiting embodiments.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Determination of the Mutual Antagonistic Effect of Strains Constituting the Composition To determine whether the individual strains do not exert an antagonistic effect on each other (inhibition of growth of some strains by others as a result of the secretion of bacteriocins into the environment), the bacteria were seeded using a sterile inoculating loop onto Petri dishes with M9 medium ($Na_2HPO_4 \times H_2O$—0.134 g; $KH_2PO_4$—0.03 g; NaCl—0.5 g; $MgSO_4 \times 7H_2O$—2.47 g; $CaCl_2$—111 mg, distilled $H_2O$ to the volume of 1000 ml) supplemented with 2-nitrophenol at a concentration of 200 mg/L (variant I) or with nutrient agar (variant II). Particular bacterial strains were seeded about 2 mm apart, in fixed configurations. The created arrangements were designated to verify whether each of the strains is able to grow in the direct vicinity of the other strains. The results were read after 24 hours of incubation at 30° C. Each of the tested strains was able to grow in direct vicinity of the other. On this basis, it can be concluded that there are no antagonistic effects between the tested microorganisms, i.e. none of the investigated strains alters the environment in such a way as to inhibit the growth of any of the others e.g. by production of bacteriocins. The same results were obtained in both variants of the experiment, which proves that also in the presence of the used xenobiotic, the investigated strains do not produce biologically active substances, which would lead to bacteriostasis.

Example 2

Determination of the Susceptibility to Antibiotics of the Strains Constituting the Composition A disc diffusion method was performed to determine the susceptibility of bacteria to the selected antibiotics. We used discs soaked with the antibiotic of a well-defined concentration (BioMerioux) (Table 2) and the minimal inhibitory concentration test was carried out, using E-tests (Oxoid) (Table 3).

TABLE 2

| Antibiotic discs used in the studies | |
|---|---|
| antibiotic | concentration [µg/ml] |
| ciprofloxacin (CIP) | 5 |
| erythromycin (E) | 15 |
| gentamicin (CN) | 30 |
| penicillin G (P) | 10 |
| streptomycin (S) | 25 |
| sulfamethoxazole (RL) | 25 |
| tetracycline (TE) | 30 |
| vancomycin (VA) | 30 |

TABLE 3

| E-tests used in the studies | |
|---|---|
| E-test (antibiotic) | E-test range [µg/ml] |
| ciprofloxacin (CI) | 32-0.002 |
| erythromycin (EM) | 256-0.016 |
| gentamicin (GM) | 256-0.016 |
| norfloxacin (NX) | 256-0.016 |
| penicillin G (PG) | 32-0.002 |
| streptomycin (SM) | 1024-0.064 |
| sulfamethoxazole (SX) | 1024-0.064 |
| tetracycline (TC) | 256-0.016 |
| ceftriaxone (TX) | 256-0.016 |
| vancomycin (VA) | 256-0.016 |

The aim of the conducted study was to determine, to what extent the isolated bacterial strains are susceptible to selected antibiotics. The antibiotics were chosen in such a way, that they belonged to different groups, respectively: aminoglycosides (gentamicin, streptomycin); second-generation fluoroquinolones (ciprofloxacin); glycopeptides (vancomycin); macrolides (erythromycin); penicillins (penicillin); sulfonamides (sulfamethoxazole); tetracyclines (tetracycline).

A McFarland's 0.5 inoculum was prepared from each strain's culture, using a densitometer (EMO). Then, using sterile cotton swabs, the suspension of bacterial cells was spread on dishes with ready-to-use MHA medium (Oxoid), and after 15 minutes, discs soaked with antibiotics at defined concentrations were placed on them.

The dishes were incubated at 25-30° C., and the results were read after 24 and 48 hours. The measure of susceptibility of a tested strain to a given antibiotic was the size of the inhibition zone which formed around the disc soaked with the antibiotic. The results read (sizes of zones measured in mm) were compared with the data contained in the European Committee on Antimicrobial Susceptibility Testing (EUCAST) standards from 2010 (Table 4).

TABLE 4

The limit values of growth inhibition zones according to EUCAST standards, 2010

| Full name of the antibiotic | Abbrev. | Antibiotic content in a disc [µg] | The limit value of growth inhibition zone (mm) S*>= | R*< |
|---|---|---|---|---|
| ciprofloxacin | CIP | 5 | 25 | 22 |
| erythromycin | E | 15 | 21 | 18 |
| gentamicin | CN | 30 | 15 | 15 |
| penicillin | P | 10 | 19 | 19 |
| streptomycin | S | 25 | 17 | 14 |
| sulfamethoxazole | RL | 25 | 16 | 13 |
| tetracycline | TE | 30 | 18 | 15 |
| vancomycin | VA | 30 | 12 | 12 |

*S - sensitive;
R - resistant

The measure of susceptibility of the tested bacterial strain to a given antibiotic was the size of the inhibition zone which formed around the disc (Table 5).

TABLE 5

Susceptibility of the tested bacterial strains to the given antibiotics, determined by disc diffusion method

| | Strain | Size of the growth inhibition zone [mm], 24 h (48 h) | | | | | | | |
|---|---|---|---|---|---|---|---|---|---|
| No | designation | RL | S | CN | CIP | TE | P | E | VA |
| 1 | 4P | 0 | 0 | 22(21) | 0 | 19(0) | 0 | 0 | 0 |
| 2 | 3G | 0 | 10 | 22(20) | 0 | 17(0) | 0 | 0 | 0 |
| 3 | 4G | 0 | 0 | 0 | 0 | 19(0) | 0 | 0 | 0 |
| 4 | 2L | 0 | 16(10) | 24(19) | 0 | 17(0) | 0 | 0 | 0 |
| 5 | 5L | 0 | 8 | 22 | 10(0) | 19(0) | 0 | 0 | 0 |
| 6 | 6L | 0 | 0 | 0 | 0 | 17(0) | 0 | 0 | 0 |
| 7 | 1N | 0 | 12(10) | 23(18) | 0 | 17(0) | 0 | 0 | 0 |
| 8 | 2N | 0 | 0 | 24(21) | 0 | 18(0) | 0 | 0 | 0 |
| 9 | 3N | 0 | 0 | 25(0) | 0 | 19(0) | 0 | 0 | 0 |
| 10 | 5N | 0 | 0 | 24 | 0 | 18(0) | 0 | 0 | 0 |
| 11 | 6N | 0 | 0 | 23(20) | 0 | 17(0) | 0 | 0 | 0 |

In the next stage of the research, MIC values of a given antibiotic for the investigated strains were determined, meaning the lowest concentration of the drug, expressed in mg/L, determined in vitro, which inhibits the growth of bacteria at a defined inoculum density, within a given time (Hryniewicz et at, 2001). These studies allow for the closer determination of the degree of susceptibility of bacteria to the applied antibiotics.

A bacterial suspension was evenly distributed on dishes with ready-to-use MHA medium (Oxoid), and then plastic testing strips (E-tests) soaked with an antibiotic with a concentration gradient were placed thereon. The dishes were incubated at 25-30° C. for 24 h, and the test results were read after this time.

The intersection of elliptical zone of inhibition, which appeared around the test strip, with the value indicator on the gradient scale of the strip, determined the lowest concentration of antibiotic, inhibiting growth of the microorganism (MIC). Similarly as in the disc diffusion method, the obtained results were compared with the guidelines contained in the relevant standards. The obtained results are shown in Table 6.

TABLE 6

MIC values of a given antibiotic for the investigated strains, determined using the E-tests

| | Strain | MIC threshold values [µg/ml] for a given antibiotic | | | | | | | | | |
|---|---|---|---|---|---|---|---|---|---|---|---|
| No | designation | SX | SM | GM | CI | TC | PG | EM | VA | NX | TX |
| 1 | 4P | 12 | 96 | 4 | ≥32 | 12 | ≥32 | 256 | — | 256 | 16 |
| 2 | 3G | ≥1024 | ≥1024 | ≥256 | ≥32 | 6 | ≥32 | ≥256 | — | 192 | ≥256 |
| 3 | 4G | ≥1024 | ≥1024 | ≥256 | ≥32 | 6 | ≥32 | ≥256 | — | >256 | ≥256 |
| 4 | 2L | 6 | 64 | 4 | ≥32 | 6 | ≥32 | ≥256 | — | 128 | ≥256 |
| 5 | 5L | 8 | 64 | 8 | 4 | 8 | ≥32 | ≥256 | — | 32 | ≥256 |
| 6 | 6L | 12 | ≥1024 | 256 | ≥32 | 6 | ≥32 | ≥256 | — | 128 | ≥256 |
| 7 | 1N | 12 | 48 | 8 | ≥32 | 6 | ≥32 | 256 | ≥256 | 96 | ≥256 |
| 8 | 2N | 12 | 384 | 8 | ≥32 | 6 | ≥32 | 128 | — | 256 | ≥256 |
| 9 | 3N | 12 | 384 | 8 | ≥32 | 6 | ≥32 | ≥256 | — | 128 | ≥256 |
| 10 | 5N | ≥1024 | 64 | 4 | ≥32 | 6 | ≥32 | 256 | — | 128 | ≥256 |
| 11 | 6N | ≥1024 | ≥1024 | 8 | ≥32 | 6 | ≥32 | 256 | — | 96 | ≥256 |

TABLE 7

E-test ranges and MIC threshold values
according to EUCAST standards, 2010

| Full name of the antibiotic | Abbrev. | E-test range [μg/ml] | MIC threshold value [μg/ml] S*>= | R*< |
|---|---|---|---|---|
| ciprofloxacin | CI | 32-0.002 | 0.5 | 1 |
| erythromycin | EM | 256-0.016 | 1 | 2 |
| gentamicin | GM | 256-0.016 | 2 | 4 |
| norfloxacin | NX | 256-0.016 | 0.5 | 1 |
| penicillin G | PG | 32-0.002 | — | 8 |
| streptomycin | SM | 1024-0.064 | 4 | 4 |
| sulfamethoxazole | SX | 1024-0.064 | 2 | 4 |
| tetracycline | TC | 256-0.016 | 1 | 2 |
| ceftriaxone | TX | 256-0.016 | 1 | 2 |
| vancomycin | VA | 256-0.016 | 2 | 2 |

*S - sensitive;
R - resistant

The MIC values determined in this study correlate with the result obtained by the disc diffusion method. The strains, for which the growth inhibition zones around discs soaked with particular antibiotic were found to be larger when compared with the other strains, were characterised by lower MIC values, meaning a lower concentration of the antibiotic that inhibits the growth of the microorganism and therefore higher susceptibility of the strain to that drug.

A comparison of MIC values with the results obtained by disc diffusion method, showed a high degree of convergence between them. With regard to the strains of bacteria, for which high MIC values have been demonstrated, growth inhibition zones around the antibiotic disc, were not observed or were very small. Such a result proves that the investigated strain is resistant to given antibiotic. The obtained MIC values were compared with MIC threshold values (Table 7) contained in EUCAST guidelines (2010). On this basis it can be stated that all of the 11 investigated strains are resistant to the antibiotics used in the study.

Example 3

Determination of the Susceptibility of the Strains Constituting the Composition to Leans Metals

TABLE 8

Heavy metal salts soluble in water

| Metal salt | Formula | Molar mass [g/mol] |
|---|---|---|
| Sodium arsenite | $NaAsO_2$ | 129.90 |
| Nickel chloride | $NiCl_2 \times 6H_2O$ | 237.70 |
| Potassium dichromate | $Cr_2K_2O_7$ | 294.20 |
| Zinc sulphate | $ZnSO_4 \times H_2O$ | 287.50 |
| Cadmium sulphate | $CdSO_4 \times 8H_2O$ | 769.54 |
| Copper sulphate | $CuSO_4$ | 159.60 |

In order to obtain the metal stock solution (concentrated) (Table 8):

100 mM water solution of salts: As(III), Cd(II), Cr(VI), Ni(II), Zn(II),

1 M water solution of Cu(II)

an aliquot of metal salt was dissolved in distilled water, then filtered through a syringe filter with a pore size of 0.22 μm. The prepared solutions were stored at 4° C. In the studies, concentrations of heavy metals in the range of 0.2-30 mM were used. For this purpose, immediately before use, a liquid medium (nutrient broth) was supplemented with an appropriate volume of the concentrated stock solution to a final concentration specified in Table 9 for each metal.

TABLE 9

The concentration range of metal salts solutions in nutrient broth

| As, Cu, Cr, Ni, Zn | 2 mM | 4 mM | 8 mM | 6 mM | 8 mM | 10 mM | 12 mM | 14 mM | 16 mM | 18 mM | 20 mM | 30 mM |
|---|---|---|---|---|---|---|---|---|---|---|---|---|
| Cd | 0.2 mM | 0.4 mM | 0.8 mM | 0.6 mM | 0.8 mM | 1.0 mM | 1.2 mM | 1.4 mM | 1.6 mM | 1.8 mM | 2.0 mM | 3.0 mM |

The susceptibility of the isolated strains to heavy metals was tested by determination of MIC values. For this purpose 96-well titration plates (ROTH) were used. 150 μl of the metal salt solution in NB was pipetted into each well, so as to create a series of increasing concentrations of each metal (gradient), then they were inoculated with 150 μl of inoculate, obtained from each strain culture, at 0.5 McFarland's density. In each of the 8 rows (12 wells) there was a different concentration of a given metal in accordance with Table 9, while the last row of microtubes was the negative control (the NB medium with saline solution, or NB with the metal stock, without inoculum).

The plates were covered with plastic caps, and additionally wrapped in cellophane foil so as to protect them from evaporation. They were incubated in a shaker (80 rev./min) at 30° C. After 24 and 48 hours of incubation, the optical densities ($OD_{600}$) of cultures were measured in each of the 96 wells. The measurements were performer using a "Sunrise" spectrophotometer (TECAN).

The values of minimal concentrations of metals inhibiting the growth of bacteria (MIC) were determined. The lowest concentration, at which no bacterial growth was observed, was considered to be the MIC value. The results are shown in Table 10.

TABLE 10

MIC values of heavy metals for the investigated strains

| No | Strain designation | MIC threshold values [mM/L], 24 h(48 h) | | | | | |
|---|---|---|---|---|---|---|---|
| | | As (III) | Cu(II) | Cr(VI) | Ni(II) | Zn(II) | Cd(II) |
| 1 | 4P | 5(6) | 3 | 1(2) | 1 | 3(5) | 0.1(0.2) |
| 2 | 3G | 5 | 3 | 1(2) | 1(2) | 4 | 0.1 |
| 3 | 4G | 5(8) | 3(4) | 1(2) | 1(2) | 4 | 0.1 |
| 4 | 2L | 4(6) | 3 | 1(2) | 1 | 3(4) | 0.1 |
| 5 | 5L | 5(7) | 3 | 1(2) | 1 | 4(5) | 0.1 |
| 6 | 6L | 5(7) | 3(4) | 1(2) | 1(2) | 4(5) | 0.1 |
| 7 | 1N | 5(8) | 3 | 1(2) | 1(2) | 4 | 0.1 |
| 8 | 2N | 5(7) | 3(4) | 1(2) | 1(2) | 3(4) | 0.1 |
| 9 | 3N | 3(5) | 3(4) | 1(2) | 1(2) | 3(4) | 0.1 |
| 10 | 5N | 4(7) | 3(4) | 1(2) | 1 | 2(4) | 0.1(0.2) |
| 11 | 6N | 4(7) | 3(4) | 1(2) | 1(2) | 2(3) | 0.1 |

TABLE 11

MIC values determined for the model strain *Escherichia coli*, according to Spain, 2003

| | | Heavy metal | MIC [mM/L] |
|---|---|---|---|
| Metal salt solutions in (NB): | As (III), Cr(VI), Ni(II), Zn(II), Cu(II): 1 mM, 2 mM, 3 mM, 4 mM, 5 mM, 6 mM 7 mM, 8 mM, 9 mM, 10 mM, 15 mM Cd(II): 0.1 mM; 0.2 mM; 0.3 mM; 0.4 mM; 0.5 mM, 0.7 mM; 0.8 mM; 0.9 mM; 1.0 mM, 1.5 mM | As(III) Cu (II) Ni (II) Zn (II) Cd (II) Cr (VI) | 0.5 1 1 1 0.5 0.2 |

The results obtained illustrate a wide variation between the MIC values for each metal. Unfortunately, in the case of cadmium it was impossible to determine the MIC. None of the investigated strains was able to grow even at the lowest concentration of cadmium salt in the culture medium, despite the use of solutions with concentration of this element an order of magnitude lower than the other metals. On this basis it can be concluded, that the toxicity of cadmium is much higher than that of the other heavy metals used in the experiment. In Table 10, the lowest cadmium salt concentration used was given as the MIC value.

The obtained results indicate that the investigated strains of bacteria are resistant to As(III), Cu(II), Cr(VI) and Zn(II), semi-susceptible to Ni(II) and susceptible to Cd(II). It should be emphasised, that in cases of arsenic and chromium, their forms considered as the most toxic to living organisms (As III and Cr VI) were used, and even so, high MIC values were recorded for all the investigated strains in comparison with the literature data for the model strain (Table 11) (Spain, 2003).

Example 4

The Method of Bioremediation of Soil Polluted with Aromatic Nitro Compounds Pure Cultures of Bacteria in a Liquid Medium Supplemented with an Aromatic Nitro Compound The aim of the experiment was to determine the growth efficiency of each of the bacterial strains in a liquid medium (M9) supplemented with an aromatic nitro compound (2-nitrophenol), being the sole carbon source for the microorganisms. The initial concentration of the nitro compound in the medium was set at 100 mg/L. All of the investigated strains showed very good growth on solid medium (M9) supplemented with the same compound, also at a doubled concentration (200 mg/L), than that used in liquid cultures.

A small volume of medium (about 20 ml) was inoculated with microbiological material (pure cultures of bacteria). Strains of bacteria isolated from the environment, grow much slower in laboratory conditions (prolonged lag-phase), because of the unknown nutritional requirements and prolonged adaptation time. Bacterial monocultures were cultivated for 7 days at room temperature with shaking on a platform shaker. During the experiment, the optical density ($OD_{600}$) of each culture was measured at daily intervals. The results are shown in Table 12.

After the experiment, the percentage change in optical density was calculated for each culture, in reference to the initial value (Table 12) with the omission of the last result (day 7, decrease in $OD_{600}$), where, most probably, the depletion of nutrients in the medium, or the accumulation of toxic secondary metabolites that inhibit the further growth of microorganisms had occurred.

TABLE 12

Growth of each of bacteria strains in liquid medium supplemented with aromatic nitro compound

| No | Strain designation | Time [days] | | | | | | Change in $OD_{600}$ [%] |
|---|---|---|---|---|---|---|---|---|
| | | 1(To) | 2 | 3 | 4 | 5 | 6 | |
| | | $OD_{600}$ | | | | | | |
| 1 | 4P | 0.215 | 0.217 | 0.276 | 0.286 | 0.295 | 0.331 | 54.0 |
| 2 | 3G | 0.139 | 0.108 | 0.174 | 0.158 | 0.177 | 0.178 | 28.1 |
| 3 | 4G | 0.124 | 0.132 | 0.173 | 0.177 | 0.184 | 0.197 | 58.9 |
| 4 | 2L | 0.205 | 0.135 | 0.150 | 0.157 | 0.179 | 0.226 | 10.2 |
| 5 | 5L | 0.190 | 0.181 | 0.215 | 0.240 | 0.243 | 0.245 | 28.9 |
| 6 | 6L | 0.250 | 0.181 | 0.262 | 0.204 | 0.234 | 0.258 | X |
| 7 | 1N | 0.162 | 0.179 | 0.184 | 0.188 | 0.190 | 0.194 | 19.8 |
| 8 | 2N | 0.176 | 0.171 | 0.225 | 0.225 | 0.230 | 0.219 | 24.4 |
| 9 | 3N | 0.170 | 0.143 | 0.219 | 0.185 | 0.191 | 0.196 | 15.3 |
| 10 | 5N | 0.220 | 0.203 | 0.220 | 0.212 | 0.230 | 0.240 | 9.1 |
| 11 | 6N | 0.130 | 0.151 | 0.175 | 0.178 | 0.180 | 0.182 | 40.0 |

The analysis of the results showed significant differences in the growth rates of the different strains. Strains 4G, 4P and 6N were characterised by the largest percentage increases in OD value, so it can be concluded that they were best-adapted to the conditions used in the experiment.

Mixed Bacterial Cultures in a Liquid Medium Supplemented with an Aromatic Nitro Compound Numerous literature data indicate that the effective degradation of aromatic nitro compounds, including mononitrophenols, requires the synergistic effect of consortia of bacteria (Nielsen et al., 2006). In accordance with the above, it was decided that mixed cultures, comprising the isolated strains of bacteria should be prepared. Mixed cultures based on these strains were started. Samples were incubated for 2 weeks. Similarly as in the previous experiment, the optical density ($OD_{600}$) of each culture was measured after 24 h. The obtained results are presented in FIG. 1, which shows the growth of mixed culture of bacteria (11 strains) in liquid medium (M9) supplemented with aromatic nitro compound.

Determination of Bioremediation Efficiency in Microcosms

Soil Preparation

The soil used in the study was collected from a depth of about 20 cm from an area not polluted with aromatic nitro compounds, located at a considerable distance from roads and factories (backyard garden).

Before the setting up of microcosms, the soil was sterilized three times in an autoclave (0.7 atm., 30 min) in order to reduce the number of indigenous microflora, which was controlled by seeding appropriate dilutions of MA extract before and after the sterilisation process.

The prepared soil was contaminated with an aromatic nitro compound, 2-nitrophenol at a concentration of 200 mg/kg of the soil. Aliquots (0.5 kg) of soil were placed in oval plastic containers and covered with lids with small holes (providing optimal oxygen conditions).

Inoculum Preparation

Bacterial inocula were prepared on the basis of strains of bacteria which are the object of the present invention, isolated from environments polluted with aromatic nitro compounds. The biomass of bacteria cell was collected from Petri dishes after applying 2 ml of saline onto them and washing off the bacterial film with a spreader. The cell suspension was quantitatively transferred into a sterile flask. Optical densities ($OD_{600}$) of the suspensions were measured. The $OD_{600}$ values of each were adjusted to a similar value of about 0.6.

Inoculation of the Soil

Soil polluted with a nitro compound (2-nitrophenol at a concentration of 1500 µg/L) was inoculated with a bacterial inoculum. The volume ratio of the inoculum to medium was 1:10, which corresponded to $10^8$ cells per 1 g of dry mass of soil. Microcosms were incubated in a darkened room at an ambient temperature of about 20° C. From time to time, the inoculated soil was mixed in order to provide proper oxygen conditions. Throughout the 30-day incubation, the moisture content was kept at approximately 50% of the water holding capacity (WHC). Lost water was replenished with an adequate volume of sterile distilled water.

Determination of Bioremediation Efficiency

The efficiency of the process of bioremediation of the soil polluted with aromatic nitro compound (2-nitrophenol) (the assessment of nitrophenol reduction in the investigated soil) was examined by carrying out measurements of concentration of the nitro compound by gas chromatography with flame ionization detector GC-FID. The determination of the content was commissioned to the "WESSLING" Laboratory of Environmental Protection (http://pl.wessling-group.com/pl/uslugi/), as was the determination of the number of bacteria.

A considerable decrease of the 2-nitrophenol content in soil (in the microcosms), as a result of biological degradation of pollutants, was observed.

The control sample (uninoculated soil) contained 2-nitrophenol at a concentration of 1500 µg/L, and subjecting it to biodegradation processes with the use of the bioremediation vaccine has led to a nearly 3-fold decline in the content of the applied nitroarene. Moreover, in the investigated experimental arrangement (apart from the control arrangement), an increase in the number of bacteria from $10^5$ cells/ml (day 1) to about $10^8$ cells/ml (day 30) was recorded.

The obtained results indicate high efficiency of the method, and the results of bioremediation on the laboratory scale, turned out to be satisfactory.

The primary objective of this solution was to develop, on the basis of the obtained strains collection, a microbiological vaccine to use in bioremediation of soil polluted with nitro compounds, as well as to assess the efficiency of the biodegradation process in microcosms.

On the basis of autochthonic microflora of the areas contaminated with aromatic nitro compounds the composition of bioremediation vaccine for land polluted with these xenobiotics was determined, and its efficiency was verified in microcosms. This stage was preceded by studies, which led to the selection of the most efficient monocultures and groups of bacteria (exhibiting the best growth on a liquid medium supplemented with an aromatic nitro compound as the sole carbon source).

The control of the process of bioremediation of polluted soil was based on physico-chemical and microbiological analyses. The effects of bioremediation in microcosms were satisfactory. After the use of bacterial inocula (a set of 11 strains), after an incubation period of 30 days, a threefold reduction in contamination was achieved with reference to the control sample (uninoculated soil). Moreover, the determination of the number of microorganisms at the beginning of the bioremediation process and following its completion, showed that the microorganisms used are characterised by a good ability to proliferate even in adverse conditions (the presence of nitroarene in the medium).

In addition, for 11 strains of bacteria included in the bioremediation vaccine, the ability to grow in the presence of high concentrations of heavy metals and antibiotics was demonstrated, and on the basis of existing standards, these strains were considered to be resistant. Considering the fact that in the polluted soils, high concentrations of not only a variety of organic xenobiotics but also of heavy metals are often reported (Bahig and Altalhi, 2009), which are considered to be potent inhibitors of organic xenobiotics biodegradation processes (Silva et al., 2007) as well as of antibiotics or their metabolites, this solution is very valuable and important for the efficiency of the process of bioremediation of soil.

BIBLIOGRAPHY

1. Bahig E. D., Altalhi A. D. 2009. Degradative plasmid and heavy metal resistance plasmid naturally coexist in phenol and cyanide assimilating bacteria. Am. J. Biochem. Biotech. 5(2): 84-93.
2. EUCAST, 2011. Clinical Breakpoint Table v. 1.3 2011-01-05. http://www.eucast.org/fileadmin/src/media/PDFs/EUCAST_files/Disk_test_documents/EUCAS T_breakpoints_v1.3_pdf.pdf.
3. Kanekar P., Doudpure P., Sarnaik S. 2003. Biodegradation of nitroexplosives. Indian J. Exper. Biol. 41: 991-1001
4. Kulkarni M., Chaudhari A. 2007. Microbial remediation of nitro-aromatic compounds: An overview. J. Environ. Manag. 85: 496-512.
5, Nielsen P. J., Dauguls A. J. 2006. Direct estimation of the oxygen requirements of *Achromobacter xyloxidans* for aerobic degradation of monoaromatic hydrocarbons (BTEX) in a bioscrubber. Biotechnol. Lett. 28: 1293-1298.
6. Schluter A., Szczepanowski R., Puhler A., Top E. M. 2007. Genomics of IncP-1 antibiotic resistance plasmids isolated from wastewater treatment plants provides evidence for a widely accessible drug resistance gene pool. FEMS Microbiol. Rev. 31:449-477.
7. Silva A. D. A., Pereira P. M., Filho S. C., Hofer E. 2007. Utilization of phenol in the presence of heavy metals by metal-tolerant non-fermentative gram-negative bacteria isolated from wastewater. Microbiol, 49: 68-73.
8. Spain A. 2003, implications of microbial heavy metal tolerance in the environment. Rev. Undergrad. Res. 2: 1-6.

The invention is further described by the following numbered paragraphs:

1. A composition of strains comprising *Stenotrophomonas* sp. strain 2L, *Stenotrophomonas* sp. strain 5L, *Stenotrophomonas* sp. strain 6L, *Stenotrophomonas* sp. strain 3N, *Achromobacter* sp. strain 4P, *Arthrobacter* sp. strain 1N, *Brevundimonas* sp. strain 2N, *Brevundimonas* sp. strain 5N, *Brevundimonas* sp. strain 6N, *Pseudomonas* sp. strain 3G, and *Pseudomonas* sp. strain 4G, deposited under the number KKP 2041p. (IAMB Collection of Industrial Microorganisms—Institute of Agricultural and Food Biotechnology in Warsaw).

2. The composition according to paragraph 1, characterised in that at least one strain of the composition, preferably all of the strains, show resistance to antibiotics from the following groups: aminoglycosides, fluoroquinolones, glycopeptides, macrolides, penicillins, sulphonamides and tetracyclines.

3. The composition according to paragraph 2, characterised in that at least one strain of the composition, preferably all of the strains, show resistance to ciprofloxacin.

4. The composition according to paragraph 2, characterised in that at least one strain of the composition, preferably all of the strains, show resistance to erythromycin.

5. The composition according to paragraph 2, characterised in that at least one strain of the composition, preferably all of the strains, show resistance to gentamicin.

6. The composition according to paragraph 2, characterised in that at least one strain of the composition, preferably all of the strains, show resistance to penicillin.

7. The composition according to paragraph 2, characterised in that at least one strain of the composition, preferably all of the strains, show resistance to streptomycin.

8. The composition according to paragraph 2, characterised in that at least one strain of the composition, preferably all of the strains, show resistance to sulfamethoxazole, 9. The composition according to paragraph 2, characterised in that at least one strain of the composition, preferably all of the strains, show resistance to tetracycline.

10. The composition according to paragraph 2, characterised in that at least one strain of the composition, preferably all of the strains, show resistance to vancomycin.

11. The composition according to paragraph 1, characterised in that at least one strain of the composition, preferably all of the strains, show resistance to heavy metals, such as As (III), Cu (II), Cr (VI), Zn (II) and Ni (II).

12. A bioremediation vaccine comprising the composition of strains as defined in paragraph 1.

13. The bioremediation vaccine according to paragraph 12, characterised in that apart from the composition of 11 strains, it comprises a liquid mineral medium supplemented with a nitro compound as the sole source of carbon.

14. The bioremediation vaccine according to paragraph 12, characterised in that apart from the composition of 11 strains, it comprises a solid mineral medium supplemented with a nitro compound as the sole source of carbon.

15. The bioremediation vaccine according to Paragraph 12, characterised in that it comprises $10^5$ bacterial cells in 1 ml of medium.

16. The bioremediation vaccine according to paragraph 13 or 14, characterised in that the nitro compound in the medium is selected from nitrobenzene, p-nitroaniline, 2-nitrotoluene, 4-nitrotoluene, dinitrotoluenes, trinitrotoluenes, mononitrophenols, polynitrophenols.

17. The bioremediation vaccine according to paragraph 13 or 14, characterised in that the source of carbon in the medium is at least one of the nitro compounds described in paragraph 16.

18. The bioremediation vaccine according to paragraph 17, characterised in that the nitro compound is added in amounts of 50-200 mg/L of the culture medium, depending on the degree of contamination of the soil.

19. Use of the bioremediation vaccine according to paragraph 12, in the removal of contaminants in the form of aromatic nitro compounds from the soil.

20. A method for the treatment of contaminated soil through the use of the vaccine, based on the isolation of soil microorganisms from the contaminated soil, their culture, then the selection/identification of the microorganisms, and then growth of the selected soil microorganisms, whereafter the propagated culture is introduced into the polluted soil, which is mechanically oxygenated and its moisture is kept at an appropriate level, characterised in that the aromatic nitro compounds are removed from the contaminated soil, and the soil microorganisms consist of the composition of strains as defined in paragraph 1.

21. The method according to paragraph 20, characterised in that it takes place in situ.

22. The method according to paragraph 20, characterised in that it takes place ex situ.

23. The method according to paragraph 20, characterised in that the cultures are propagated on a liquid mineral medium supplemented with a nitro compound as the sole source of carbon.

24. The method according to paragraph 20, characterised in that the cultures are propagated on a solid mineral medium supplemented with a nitro compound as the sole source of carbon.

25. The method according to paragraph 23 or 24, characterised in that the nitro compound in the medium comprises nitrobenzene, p-nitroaniline, 2-nitrotoluene, 4-nitrotoluene, dinitrotoluenes, trinitrotoluenes, mononitrophenols, polynitrophenols.

26. The method according to paragraph 23 or 24, characterised in that the source of carbon in the medium is at least one of the nitro compounds described in paragraph 25.

27. The method according to paragraph 20, characterised in that the nitro compound is added in amounts of 50-200 mg/L of the culture medium, depending on the degree of contamination of the soil.

28. The method according to paragraph 20, characterised in that the culture is propagated at temperatures between 20-25° C.

29. The method according to paragraph 20, characterised in that the contaminated soil is sprayed with the suspension of bacteria (bioremediation vaccine) in volume ratio of the vaccine to soil in the range of 1:10 to 3:10.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A method of treating soil contaminated with aromatic nitro compounds comprising contacting the contaminated soil with a composition comprising a mixture of *Stenotrophomonas* sp. strain 2L, *Stenotrophomonas* sp. strain 5L, *Stenotrophomonas* sp. strain 6L, *Stenotrophomonas* sp. strain 3N, *Achromobacter* sp. strain 4P, *Arthrobacter* sp. strain 1N, *Brevundimonas* sp. strain 2N, *Brevundimonas* sp. strain 5N, *Brevundimonas* sp. strain 6N, *Pseudomonas* sp. strain 3G, and *Pseudomonas* sp. strain 4G, deposited under the number KKP 2041p, IAFB Collection of Industrial Microorganisms—Institute of Agricultural and Food Biotechnology in Warsaw.

2. The method of claim 1 further comprising mechanically oxygenating, and maintaining a moisture level in, the soil.

3. The method according to claim 1, wherein the method is performed in situ.

4. The method according to claim 1, wherein the method is performed ex situ.

5. The method according to claim 1 wherein the contacting comprises spraying the soil with the composition in a volume ratio of the composition to soil in the range of 1:10 to 3:10.

6. The method of claim 1, wherein at least one strain of the composition shows resistance to antibiotics, wherein the antibiotics are aminoglycosides, fluoroquinolones, glycopeptides, macrolides, penicillins, sulphonamides or tetracyclines.

7. The method of claim 6, wherein at least one strain of the composition shows resistance to ciprofloxacin.

8. The method of claim 6, wherein at least one strain of the composition shows resistance to erythromycin.

9. The method of claim 6, wherein at least one strain of the composition shows resistance to gentamicin.

10. The method of claim 6, wherein at least one strain of the composition shows resistance to penicillin.

11. The method of claim 6, wherein at least one strain of the composition shows resistance to streptomycin.

12. The method of claim 6, wherein at least one strain of the composition shows resistance to sulfamethoxazole.

13. The method of claim 6, wherein at least one strain of the composition shows resistance to tetracycline.

14. The method of claim 6, wherein at least one strain of the composition shows resistance to vancomycin.

15. The method of claim 1, wherein all of the strains show resistance to aminoglycosides, fluoroquinolones, glycopeptides, macrolides, penicillins, sulphonamides and tetracyclines.

16. The method of claim 1, wherein at least one strain of the composition, shows resistance to heavy metals, wherein the heavy metal is As (III), Cu (II), Cr (VI), Zn (II) or Ni (II).

17. The method of claim 16, wherein all of the strains show resistance to As (III), Cu (II), Cr (VI), Zn (II) and Ni (II).

18. The method of claim 1, wherein the composition further comprises a liquid mineral medium supplemented with a nitro compound as the sole source of carbon.

19. The method according to claim 1 further comprising a solid mineral medium supplemented with a nitro compound as the sole source of carbon.

20. The method of claim 18, wherein the composition comprises $10^5$ bacterial cells in 1 ml.

21. The method of claim 18, wherein the nitro compound is nitrobenzene, p-nitroaniline, 2-nitrotoluene, 4-nitrotoluene, a dinitrotoluene, a trinitrotoluene, a mononitrophenol, or a polynitrophenol.

22. The method of claim 19, wherein the nitro compound is nitrobenzene, p-nitroaniline, 2-nitrotoluene, 4-nitrotoluene, a dinitrotoluene, a trinitrotoluene, a mononitrophenol, or a polynitrophenol.

23. The method according to claim 21 wherein the nitro compound is present in amounts of 50-200 mg/L of the medium.

24. The bioremediation mixture according to claim 22 wherein the nitro compound is present in amounts of 50-200 mg/L of the medium.

25. The method according to claim 18 wherein the soil is sprayed with the composition in a volume ratio of the composition to soil in the range of 1:10 to 3:10.

26. The method according to claim 19 wherein the soil is sprayed with the composition in a volume ratio of the composition to soil in the range of 1:10 to 3:10.

* * * * *